(12) United States Patent
Inoue et al.

(10) Patent No.: US 6,436,447 B1
(45) Date of Patent: Aug. 20, 2002

(54) EVACUANT

(75) Inventors: Ranko Inoue; Takeshi Inoue; Seiichi Yamagiwa, all of Tokyo (JP)

(73) Assignee: Fujix, Inc., Tokyo (JP)

( * ) Notice: Subject to any disclaimer, the term of this patent is extended or adjusted under 35 U.S.C. 154(b) by 0 days.

(21) Appl. No.: 09/447,217

(22) Filed: Nov. 23, 1999

(30) Foreign Application Priority Data

Nov. 26, 1998 (JP) ............................................ 10-334834
Jun. 4, 1999 (JP) ............................................ 11-158265
Aug. 30, 1999 (JP) ............................................ 11-242369

(51) Int. Cl.$^7$ .......................... A61K 33/08; A61K 9/20; A61K 9/00; A61K 9/14; A61P 1/10

(52) U.S. Cl. ........................ 424/692; 424/400; 424/439; 424/451; 424/464; 424/466; 424/489; 424/499; 424/93.1; 424/93.3; 424/93.4; 424/93.45; 424/93.51; 424/195.16; 424/780; 514/23; 514/53; 514/470; 514/557; 514/819; 514/892; 514/925; 514/951; 514/952

(58) Field of Search ................................. 424/692, 489, 424/499, 466, 93.45, 93.4, 400, 439, 451, 464, 93.1, 93.3, 93.51, 195.16, 780; 514/470, 23, 53, 557, 951, 952, 819, 892, 925

(56) References Cited

U.S. PATENT DOCUMENTS 4,458,030 A * 7/1984 Manabe et al. .............. 502/183

FOREIGN PATENT DOCUMENTS

JP        09 040561 A      2/1997

OTHER PUBLICATIONS

AHFS 94 Drug Information, American Society of Hospital Pharmacists, Maryland, pp. 1870–1874, 1994.*
Calis S. et al.: "In vitro adsorption of propranolol hydrochloride by various antacids", Drug Development and Industrial; Pharmacy vol. 12, No. 11–13, 1986, pp. 1833–1845, XP000892398.
Miyasaka K. et al.: "A modified penetration rate method for measuring the wettability of magnesium oxide powders", Chemical and Pharmaceutical Bulletin, vol. 24, No. 2, 1976, pp. 330–336, XP002133697.
Database WPI Section Ch, Week 199716 Derwent Publications Ltd., London, GB; Class A96, AN 1997–175601, XP002133698 (1997).
Rizkalla N. et al.: "Influence of the fractal character of model substances on their reactivity at solid–liquid interfaces", Journal of Colloid and Interface Science vol. 215, No. 1, Jul. 1999, pp. 43–53, XP000892572.

* cited by examiner

Primary Examiner—John Pak
(74) Attorney, Agent, or Firm—Armstrong, Westerman & Hattori, LLP

(57) ABSTRACT

Disclosed is an evacuant possessing a sufficient evacuating effect in a small dose substantially without accompanying any irritation to bowel, irrespective of whether its preparations are in the form of tablets, liquids or elixirs, and having a suppressing action to odor of feces. This evacuant is characterized by containing an active magnesium oxide which has a BET value (surface area in terms of $m^2/g$) of at least 21, preferably 21–50, more preferably 30–40 and is excellent in acid reactivity, and may preferably be incorporated with lactic acid bacteria, a mixture of sporolactobacteria and yeast extracts and/or oligosaccharides. The preparations are preferably in the form of liquids, granules, tablets and capsules.

25 Claims, 2 Drawing Sheets

FIG. 2

INFLUENCE OF MAGNESIUM OXIDE ON WET WEIGHT OF FECES OF RATS

EVACUANT

BACKGROUND OF THE INVENTION

The present invention relates to an evacuant utilizable for constipation or evacuation of bowel contents, and more particularly, it relates to an evacuant of magnesium type possessing a satisfactory evacuating effect in a smaller dose substantially without accompanying irritation to bowel unlike a conventional evacuant of magnesium type heretofore known to exhibit evacuating effect only in a relatively large dose.

From the past, known as an evacuant are tablets or semi-liquid preparations comprised of magnesium oxide or magnesium hydroxide as a main ingredient and incorporated with a binding agent, a disintegrating agent, etc. In case of evacuants of this type, however, it was necessary to take them in a greater dose increased in its weight for achieving a satisfactory evacuating effect so that it was very inconvenient to take such a greater dose of the evacuant. Such conventional evacuant irritates bowel to cause peristalic movement for acceleration of evacuating action, thus resulting in side-effects such as bellyache and intestinal damage for the sake of long-term administration. It can hardly be said therefore that conventional evacuants are taken safely for health.

In order to solve these-problems, the present inventors already developed an evacuant comprises of magnesium oxide, a binder capable of displaying evacuating effect and a disintegrating agent capable of exhibiting evacuating effect and applied for a patent (Japanese Laid-open Patent Appln. No. Hei. 9-40561).

As a result of the present inventors further research made by tracing the gist of the above patent application for developing a more effective evacuant which is reduced in its weight for facilitating oral administration, it has now been found surprisingly that an evacuant containing magnesium oxide of a specific BET value (unit: $m^2/g$; referred to hereinafter simply as "BET value"; this BET value is well understood as "surface area" of a solid substance such as a solid catalyst and can be measured according to the so-called BET method using a gas adsorption for determination of a catalyst activity) as an effective ingredient shows an excellent acid reactivity as well as a selectively good evacuating effect and possesses an activity for promoting evacuating action without accompanying any side-effect even after administration for a long period of time, unlike preparations widely utilizable as an evacuant from the past which irritate bowel directly. The present invention has been accomplished on the basis of the above finding.

SUMMARY OF THE INVENTION

It is an object of the present invention to provide an evacuant easily capable of oral administration which exhibits an evacuating effect satisfactorily in a smaller dose without irritating bowel.

It is another object of the present invention to provide an evacuant capable of making the action of good (character) bacteria prevailing to keep the environment of bowel well thereby extremely suppressing odor of feces or stool, which comprised of the aforesaid specific magnesium oxide incorporated with lactic acid bacteria, especially a mixture of sporolactobacteria such as *Sporolactobacillus inulinus* and an yeast extracts and/or an oligosaccharide.

Other and further objects, features and advantages of the present invention will become apparent more fully as the description proceeds.

BRIEF DESCRIPTION OF THE DRAWINGS

FIG. 2 is a graph showing wet weights of feces collected at every observing period of time in Example 1 and Comparative Example 1, wherein solid lines show a result of Sample A (Example 1) while dotted lines show a result of Sample B (Comparative Example 1).

DETAILED DESCRIPTION OF PREFERRED EMBODIMENTS OF THE INVENTION

Figure 1:
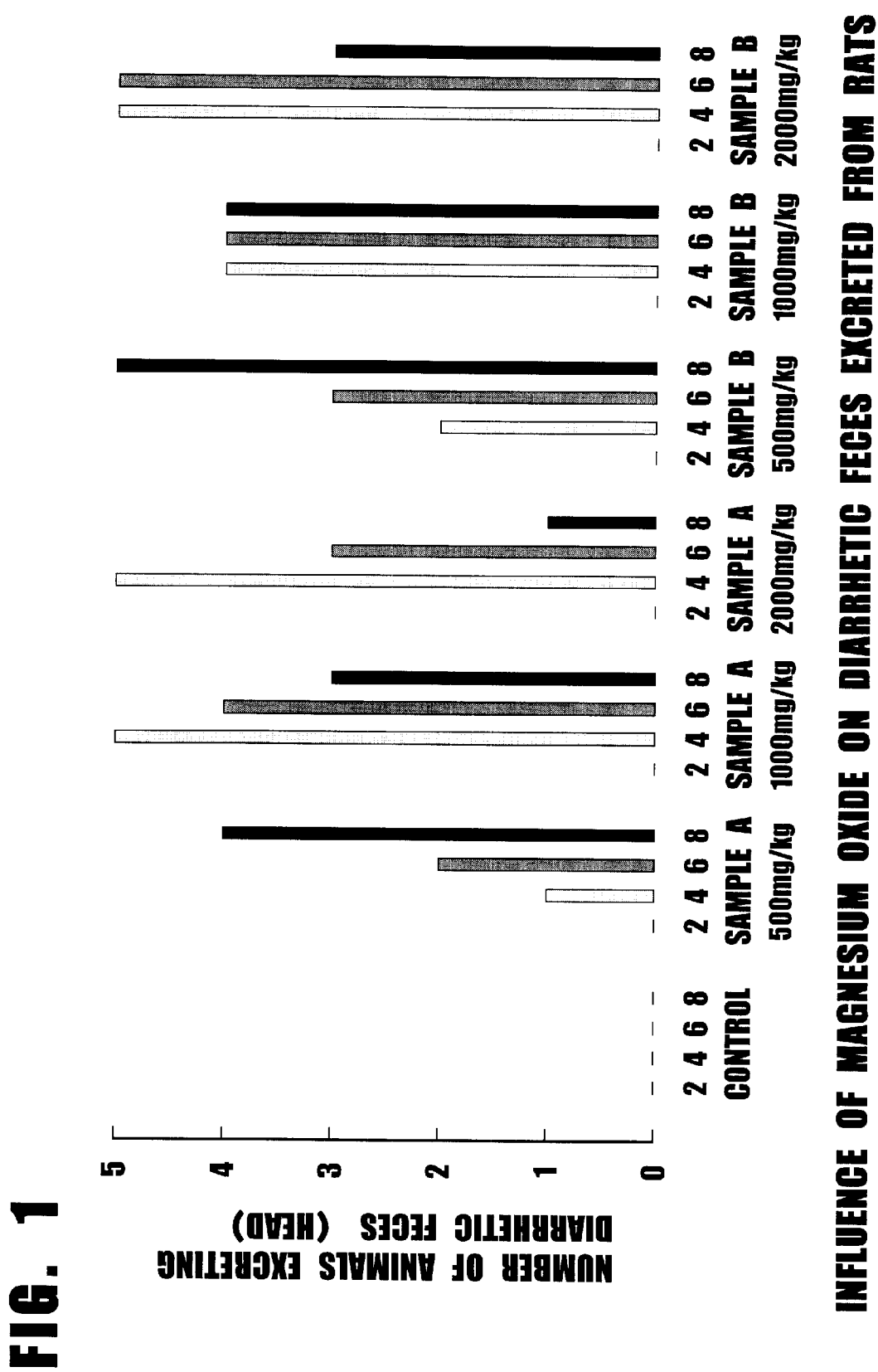
FIG. 1 is a graph showing a result of tests in Example 1 wherein the influence of magnesium oxide on diarrhetic feces is investigated by using animals excreting feces on a score of at least 2 and observing them at every observing period of time (0–2, 2–4, 4–6 and 6–8 hours).

The present invention has been proposed for achieving the aforesaid objects and has an important characteristic feature in selection of magnesium oxide having a specific BET value as an effective ingredient of the evacuant.

In accordance with the present invention, there is provided an evacuant comprising magnesium oxide having a BET value of at least 21 as an effective ingredient thereof. It is preferable that the BET value of the magnesium oxide is in the range from 21 to 51. It is especially preferable that the BET value of the magnesium oxide is in the range from 30 to 40.

In accordance with the present invention, there is also provided the afore-said evacuant further containing lactic acid bacteria.

In accordance with the present invention, there is further provided the afore-said evacuant wherein the lactic acid bacteria are at least one of bifidobacteria such as *Bifidobacterium bifidum* and *longum*, at least one lactobacteria selected from *Lactobacillus lactis, lactobacillus acidophilus, Lactobacillus salivalius* and *Lactobacillus fermentium* and/or sporolactobacteria of these involving *Sporolactobacillus inulinis*.

In accordance with the present invention, there is still further provided the aforesaid evacuant wherein the sporolactobacteria are in mixture with yeast extracts.

In accordance with the present invention, there is still further provided the aforesaid evacuant further containing oligosaccharides.

In accordance with the present invention, there is still further provided the aforesaid evacuant which is in the form of a liquid preparation dissolved in an L-form fermentation lactic acid.

In accordance with the present invention, there is still further provided the aforesaid evacuant in the form of powders or granules obtained by a dry or wet granulation method, or tablets obtained by compressing these powders or granules.

In accordance with the present invention, there is still further provided the aforesaid evacuant in the form of capsule preparations obtained by charging capsules with the powders or granules obtained by a dry or wet granulation method.

In accordance with the present invention, there is still further provided the aforesaid evacuant wherein the wet granulation method employs an alcohol.

In accordance with the present invention, there is still further provided the aforesaid evacuant wherein an oral refresher is further incorporated therewith.

Below is an explanation on the practical embodiment of the present invention.

One of the greatest technical feature of the present invention resides in the use of magnesium oxide having a BET value of at least 21 as effective ingredient of the evacuant.

The magnesium oxide used in the present invention should have a BET value of at least 21 and may usually have a BET value of about 150, but preferably has a BET value within the range from 21 to 150. More preferably is magnesium oxide having a BET value of 30–40.

As is confirmed by results of Examples given hereinafter, a specific magnesium oxide having a BET value of at least 21 taken up in the present invention exhibits an excellent evacuating effect owing to its superior active acid-reactivity. This magnesium oxide used in the present invention is referred to herein as "active magnesium oxide" to distinguish itself from the ordinary magnesium oxide.

From the past, an evacuant containing magnesium oxide or magnesium hydroxide as a main ingredient thereof is known. Above all, an evacuant comprised predominantly of magnesium hydroxide is most widely utilizable.

If comparison is made in term of MgO content, the same effect as obtained by 100% magnesium hydroxide is obtained in case of magnesium oxide in an amount of about 70% of the magnesium hydroxide. However, a problem arises in case of magnesium oxide because of its strong hygroscopic property so that it becomes unstable at the stage of manufacturing pharmaceutical preparations thus making it difficult to manufacture homogeneous preparations.

Magnesium oxide is generally prepared from sea water according to the following chemical equation standing for the reaction between bittern and lime to form magnesium hydroxide and then by baking it.

$$MgCl_2 + Ca(OH)_2 = Mg(OH)_2 + CaCl_2$$

$$Mg(OH)_2 \rightarrow (baking) \rightarrow MgO$$

The BET value of magnesium oxide is almost determined by the baking temperature of magnesium hydroxide or magnesium carbonate in the process of preparation. If the baking temperature is about 800° C., the BET value will exceed 50 while the baking temperature exceeds 1000° C., for example, at about 1200° C., the BET value will become 20 or less [Chem. Pharm. Bull. 24 (2), 330–336 (1976), especially Table 1 referred to]. If the temperature for baking magnesium hydroxide is lower, the resultant light magnesium oxide will become porous and larger in surface area so that it will be suited for the active magnesium oxide used in the present invention. On the other hand, if magnesium hydroxide is baked at a temperature higher than 1000° C., the resultant MgO will be coagulated to form a heavy magnesium oxide of a dense structure having a smaller surface area so that it becomes lower in acid reactivity and evacuating effect.

The reason why magnesium oxide displays an effect as an evacuant is ascribable to the mechanism as will be described below.

When magnesium oxide is orally administered, it will firstly react with an acid in the stomach to form magnesium chloride according to the following equation:

$$MgO + 2HCl = MgCl_2 + H_2O$$

The resultant magnesium chloride is then neutralized at the rear part of duodenum with pancreatic juice secreted from pancreas, which contains sodium bicarbonate, whereby the magnesium chloride is converted into magnesium bicarbonate to increase a pH value according to the following formula:

$$MgCl_2 + 2NaHCO_3 \rightarrow Mg(HCO_3)_2 + 2NaCl$$

Successive to the above conversion, the neutral magnesium bicarbonate initially formed [$Mg(HCO_3)_2$] is gradually converted into basic magnesium carbonate as the sodium bicarbonate moves from the small intestine to the colon. As the basic magnesium carbonate is converted to have such a structure that water is contained in its molecule, the magnesium salt functions to prevent effluence of water from bowel. It is presumed therefore that feces become soft and gain the volume thereof by such conversion so that an evacuation effect is exhibited without bellyache.

Considering such effect, it follows that the evacuating effect is influenced by how the basic magnesium carbonate carrying molecules of water, which is formed by the reaction of magnesium oxide (in the form of magnesium chloride) with sodium bicarbonate in bowel, is produced in a larger amount. Thus, important is how the magnesium oxide is rapidly and in a larger amount converted in stomach into magnesium chloride. Since the active magnesium oxide used in the present invention has a larger BET value, its acid reactivity with acids in the stomach becomes faster to make it suited as an evacuant.

In general, the activity of magnesium oxide becomes higher as the BET value becomes larger. Accordingly, to have a high activity means that the evacuating effect becomes good. As the MgO content becomes too high to be suited as a medicament, however, MgO having a BET value of 21–50 is utilized preferably. On the other hand, if MgO has a BET value not more than 20, sintering of its crystals is excessively promoted to become hard and inferior in acid reactivity so that the evacuating effect becomes poor as is evident from Comparative Example 1 given hereinafter wherein a wet weight of feces is small. It is presumed that the active magnesium oxide adopted in the present invention having a BET value of at least 21 is of a porous or microporous surface so that this surface character makes its acid reactivity outstanding to bring about activity to magnesium oxide.

If the BET value becomes larger than 21, especially at least 25, the surface area of magnesium oxide will be greater so that it will become fine powders having a high hygroscopic property, thus making it difficult to be processed to pharmaceutical preparations. However, difficulty in processing to pharmaceutical preparations may be solved by incorporating the preparations with a disintegrating agent or a binding agent such as carboxymethylcellulose calcium, hydroxypropylcellulose of a low substitution, crystalline cellulose, etc.

The fact that the active magnesium oxide of the present invention exhibits an excellent effect as evacuant has been confirmed as a result of experiments made for a long period of time using rats and as a result of repeated administration to human on the basis of the result of the animal experiments. A pharmacological principle of the evacuating effect is considered to be ascribable to the fact that magnesium salt is converted in bowel into insoluble basic magnesium carbonate thereby increasing enteral osmotic pressure to store water, thus displaying evacuating effect.

The BET value of the active magnesium oxide in the present invention is determined by seeking suitable characteristics for evacuant such as obstacles for manufacturing preparations, purity as pharmaceutical regulations, evacuating effect, and hygroscopic property, and summing up these results.

The evacuant of the present invention can improve environment of bowel and can extremely suppress odor of feces or stool without affecting evacuating effect by incorporating the preparations with lactic acid bacteria, especially a mixture of yeast extracts and sporolactobacteria such as Sporolactobacillus inulinus which is acid- and alkali-resistant and capable of making good (character) bacteria prevail thereby improving environment of bowel.

It is generally known to take lactic acid bacteria for adjusting conditions of digestive organs. However, a substantial proportion of ordinary lactic acid bacteria is known to become extinct by the action of acid in the stomach so that it is quite unavoidable that only a limited proportion of lactic acid bacteria taken reaches bowel. In order to prevent such circumstances, it is proposed to pack capsules with lactic acid bacteria, but such proposal is less economical at cost and so gain in the amount is only limited to the volume of capsules. Thus, it is difficult to enter lactic acid bacteria in a perfect condition in digestive organs.

Since the active magnesium oxide which is a main ingredient of the evacuant of the present invention functions to neutralize acid in the stomach to increase a pH value thereof, however, lactic acid bacteria as so-called good (character) bacteria incorporated into the active magnesium oxide can safely reach in a perfect condition to bowel without extinction on the way. Further, so-called bad (character) bacteria capable of generating indole or skatole which a source of bad odor in feces can be extirpated by acids secreted from so-called good (character) bacteria so that bad odor of excreted feces can extremely suppressed.

No limitation exists in the sort of lactic acid bacteria so far as they are called good (character) bacteria. In particular, at least one bifidobacillus such as *Bifidobacterium bifidum, Bifidbacterium longum*, at least one lactic acid bacteria selected from *Lactobacillus lactis, Lactobacillus acidophilus, Lactobacillus salivalius*, and *Lactobacillus fermentium*, and sporolactobacteria of these bacteria such as Sporolactobacillus inulinus, especially, a mixture of such sporolactobacteria and yeast extracts are preferably used.

By the term sporolactobacteria or sporolactobacillus is meant a bacteria or bacterium wherein spores are formed around lactic acid bacteria. In general, spores are not formed during lactic acid bacteria are actively grown, but budding of spores is considered to begin when a period of logarithmic propagation of nutrient cell colonies has passed due to shortage of nutrients. These sporolactobacteria possess high resistance to heat, ultra-violet rays, electrolytic radiation, and various toxic compounds in addition to acid- and alkali-resistance.

Spores formed around sporolactobacteria are split off under the condition of a pH value of 6.8 above 30° C. and initiate action as lactic acid bacteria. Accordingly, the evacuant of the present invention comprising active magnesium oxide containing sporolactobacteria is stable until it reaches bowel after oral administration. When a pH value in bowel is changed to almost neutral by the action of magnesium oxide, the spores of the sporolactobacteria are split off by influence of body temperature and initiate the action of lactic acid bacteria which are roughly accounted as one hundred million per gram.

It is preferable that the sporolactobacteria are employed as a mixture with yeast extracts as feed to promote growth of lactic acid bacteria. In a mixture of the sporolactobacteria with yeast extracts, the sporolactobacteria are usually contained in an amount of about 1% and the remaining components contained are almost lactose and oligosaccharides. In some cases, collagen, ginseng, etc. may be contained in the remaining components. The aforesaid mixture of sporolactobacteria with yeast extracts is also acid- and alkali-resistant so that a conjoint use of the mixture with active magnesium oxide does not induce deceleration of evacuating effect but rather render the action of good (character) bacteria prevailing to keep environment of bowel good.

As the number of senile people henceforth becomes larger, the number of good (character) bacteria living in bowel of such senile people is presumed to decrease. Considering this situation, the conjoint use of magnesium oxide having a proper BET value as an evacuant with a mixture of sporolactobacteria with yeast extracts is said to be desirable even in daily life.

A proportion of the lactic acid bacteria to be incorporated into the evacuant of the present invention is 10–40% by weight, preferably 20–30% by weight.

The evacuant of the present invention is preferably incorporated with an aligosaccharide. As an oligosaccharide per se has an evacuating effect, it is desirable to use the oligosaccharide as an excipient in case of tableting so that the amount of magnesium oxide which is difficult to be taken can be decreased to reduce the amount of administration. In addition, an oligosaccharide is one of the edible fibers, which displays a synergistic effect of propagating bifidobacteria as the oligosaccharide is not digested in digestive organs in human and becomes feed for good (character) bacteria in bowel and decreasing the number of bad (character) bacteria. Thus, the aligosaccharide can contribute to keep the environment of bowel good as in the case of lactic acid bacteria.

A proportion of the oligosaccharide in the evacuant of the present invention is 5–20% by weight, preferably 10–15% by weight.

In manufacturing preparations of the evacuant of the present invention, the evacuant is incorporated with a disintegrating agent and a binding agent, both agents being capable of exhibiting the evacuating effect. Illustrative of the disintegrating agent are, for example, carboxymethylcellulose calcium, carboxymethylcellulose, and a lower substituted hydroxypropylcellulose. Above all, carboxymethylcellulose is registered as an evacuant under the Japanese Pharmacopoeia and is recognized by the Japanese Pharmaceutical Law. Among these, the disintegrating agent may be used singly or in combination of at least two. Considering the reason that reactivity of magnesium oxide with acids in the stomach is to be promoted, a proportion of the disintegrating agent is 5–20% by weight, preferably 5–10% by weight per tablet.

Illustrative of the binding agent utilizable for the present invention are, for example, carboxymethylcellulose sodium, a lower substituted hydroxypropylcellulose, and crystalline cellulose. Among these, carboxymethylcellulose sodium is registered as an evacuant under the Japanese pharmacopoeia and is recognized by the Japanese Pharmaceutical Law. Among these compounds, the binding agent may be employed singly or in mixture of at least two. A proportion of the binding agent is 1–10% by weight, preferably 1–5% by weight per tablet of the evacuant for the reason of necessity for good granule-shaping and of obtaining good tablets.

A technical feature of another embodiment of the present invention resides in incorporation of the aforesaid evacuant with phenolphthalein. In this embodiment, the evacuant incorporated with phenolphthalein becomes pink in tint gives users good feeling in visual sense. As phenolphthalein per se exhibits an evacuating effect, the evacuant incorporated with phenolphthalein can be enhanced in evacuating effect.

In the present invention, the proportion of phenolphthalein is 0.01–1% by weight, preferably 0.01–0.05% by weight per tablet of the evacuant, in order to attain a dual action of evacuating effect and coloring in pink to red aiming at visually good feeling.

A technical feature of still another embodiment of the present invention resides in incorporation of the aforesaid evacuant with an oral refresher. The evacuant incorporated with an oral refresher can fill the mouth with a refreshing flavor to render the users refreshing feeling.

Illustrative of the oral refresher used in the present invention are, for example, jintan, peppermint and a similar material such as spearmint. In the present invention, a proportion of the oral refresher is 0.01–0.1% by weight, preferably 0.01–0.05% by weight per tablet of the evacuant.

The evacuant of the present invention can be prepared in any of the types known per se. In particular, the evacuant is supplied preferably in the form of a liquid or solution preparations, granules, tablets, and capsules.

In case the evacuant of the present invention is used in liquid preparations, the evacuant containing active magnesium oxide is dissolved in an acid capable of dissolving the evacuant. It is most preferable to use L-form fermentation lactic acid as the acid for preparing liquid preparations. As compared with DL-form fermentation lactic acid, the L-form fermentation lactic acid can dissolve active magnesium oxide completely so that the resultant liquid preparations become a transparent solution. Moreover, the liquid preparations are excellent in taste sense on oral administration so that the preparations are easy to be drunk for senile persons who are difficult to take tablets or capsules. Further, the active magnesium oxide is rapid in acid reactivity, thus shortening a period of time needed for manufacturing the preparations. In addition, the use of L-form fermentation lactic acid has a superior merit that the formation of a precipitate does not take place in case of using DL-form fermentation lactic acid.

In the present invention, the aforesaid liquid-type evacuant is incorporated with an oligosaccharide whereby an excellent merit can be achieved in that the inherent evacuating effect is further enhanced and mild sweetness of the oligosaccharide promotes oral administration of the evacuant. A conventional liquid-type evacuant known hitherto contains predominantly magnesium hydroxide and is in the form of a white gruel so that it is rather difficult to take. In contrast, the liquid-type evacuant of the present invention incorporated with the fermentation lactic acid and an oligosaccharide is significantly improved in easiness in oral administration and in evacuating effect.

In case the evacuant of the present invention is processed to preparations, magnesium oxide is of high moisture-absorbing property when pulverized to microfine powders so that it cannot be subjected to a direct tableting treatment. However, the evacuant may be subjected to a dry granulation treatment and then to a tableting treatment. In case of a wet granulation treatment, the evacuant may be treated with an alcohol and then subjected to the wet granulation treatment. Tablets of the evacuant can be manufactured by subjecting the resultant granules to a tabuleting treatment Another preferable preparations of the evacuant of the present invention are in the form of capsules, such as gelatin capsules, packed with a powdery or granular evacuant. Considering workability of capsulation, it is preferable to pack capsules with the granular evacuant. Mentioned as a method of capsulation are, for example, the so-called Auger method wherein capsules are packed under pressure with a powdery solid by means of a spiral screw, Compress method wherein a powdery solid is packed under pressure by the aid of a compressing plunger, and Disk method wherein a powdery solid is compressed taking advantage of its fluidity under natural gravity flow or by compulsory vibration.

Magnesium oxide employed at present for hospitals or drug stores is of a BET value of about 20. Aiming at an active magnesium oxide having a BET value of about 40 and a higher acid reactivity than the magnesium oxide having a BET value of about 20, a test for evaluating evacuating effect has been carried out by using these magnesium oxide samples for rats.

In the undermentioned Example 1 illustrates a result of the test for rats by using an active magnesium oxide having a BET value of 40, while a result of a similar test for rats by using a magnesium oxide having a BET value of 20 is illustrated in Comparative Example 1 given hereunder.

Effect of the Invention

According to the present invention, there is provided an evacuant which is suitable for oral administration and exhibits even in a smaller dose a satisfactory and smooth evacuating effect without any irritation to bowel.

The evacuant of the present invention which is rapid in acid reactivity can exhibit a sufficient evacuating effect usually at one time administration before sleeping, and moreover brings about effective evacuating effect without any side effect for senile persons weakened in their function of bowel since vermicular motion of bowel dose not take place by administration of the evacuant. Accordingly, the evacuant of the present invention is advantageous in aspect of effectively utilizing for senile persons as compared with a conventional evacuant which causes vermicular motion of bowel.

In case the evacuant of the present invention is incorporated with lactic acid bacteria called good (character) bacteria, especially a mixture of sporolactobacteria with yeast extracts, lactic acid bacteria including sporolactobacteria reach efficiently to bowel without being perished in stomach by a neutralizing effect of magnesium oxide, and extirpate acid-weak bad (character) bacteria in bowel by acids secreted by these good (character) bacteria so that bad odor is scarcely felt in excreted feces.

In case the evacuant of the present invention is incorporated with an oligosaccharide, a dose of the evacuant can be decreased and a dual action of enhanced evacuating effect and easiness in oral administration can be attained if the evacuant is in the form of liquid preparations, thus significantly contributing to improvement of environment in bowel.

EXAMPLES

The present invention will now be illustrated in more detail by way of Examples and Comparative Examples.

Example 1

Prescription. of Ingredients:

| | |
|---|---|
| Active magnesium oxide (BET value: 40) | 86.5% by weight |
| Carboxymethylcellulose calcium | 10.0% by weight |
| Carboxymethylcellulose sodium | 1.0% by weight |
| Magnesium stearate (a lubricating agent) | 2.5% by weight |

<Method for Producing Preparations>

Among the aforesaid ingredients, magnesium stearate was omitted and the remaining ingredients were all extruded and brought into an agitation-granulating machine where the mixture was kneaded with 99% alcohol and extruded through a metal mesh of 0.7 mm to manufacture granules of the mixture. After drying the granules overnight at 80° C., the resultant dry granules were screened to have a size of 20–80 mesh, mixed with magnesium stearate and thereafter the mixture was subjected to a tab treatment by the aid of a rotary tableting machine operated under the following tableting conditions whereby white tablets were obtained without being darkened in appearance. The resultant tablets are arbitrarily referred to as Sample A. Tableting conditions:

Pestle diameter: 18 mm Weight of tablets: 318 mg

Tableting pressure: (preliminary pressure) 300 kg; (real pressure) 600 kg

Hardness: 11 kg Disintegrating time: 22 sec.

Comparative Example 1

In Example 1, a similar treatment was carried out except that magnesium oxide having a BET value of 20 was used in place of the active magnesium oxide. The resultant tablets are arbitrarily referred to as Sample B.

<Confirmation of Evacuating Effects>

Preparation of Substances to be Tested:

The Samples A and B were pulverized and suspended in water for injection (manufactured by Ohtuka Pharmaceutical Ind., Co.; Lot no. K6E83) to prepare test samples.

Animal Used for the Test:

Using Slc:Wistar male rats of 9 weeks old (available from Nihon SLC Co., Japan) were forced to take freely a solid feed (Labo-MR stock; available from Nihon Nohsan Kogyo Co., Japan) and tap water and subjected to a preliminary feeding for at least one week including a period of quarantine under the circumstances of a temperature of 22±2° C., a humidity of 55±15%, a illumination time of 8:00–20:00 and a number of ventilation of 13–17 times/hour. Thereafter, rats for which no abnormal symptom was detected in ordinary state were used as test animals.

Testing Method:

A number of feces during one night from the day before the test to the just very day for the test was investigated for confirming that no animal excreting diarrhetic feces was found among the test animals. Each test sample was orally administered to the animals of 10 weeks old (body weight: 218–252 g) at a rate of 10 ml/kg in accordance with the table for group construction given hereunder. The test animals were then entered individually in cages and a filter paper (26×20 cm) the dry weight of which was previously measured was laid on a feces-receiving dish positioned on the bottom of each cage. With respect to feces excreted on the filter paper, symptom of diarrhea, the number of feces, and appearance of feces was observed and simultaneously the water contents of feces was measured. A test for appearance of feces was carried out according to the items shown in the table below and a score of the observation was evaluated and recorded. The measurement of water contents of feces was carried out by collecting feces together with the filter paper at the time of observation, measuring its weight as wet weight (W), drying the filter paper for 3 days at 50° C. after measurement of the wet weight, measuring its weight as dry weight (D) and calculating the water contents according to the equation given hereunder.

Feces having a score number of at least 2 was determined as diarrhetic feces and the number of animals excreting diarrhetic feces was counted in order to calculate a 50% effective dose for evacuation ($ED_{50}$) and a 80% effective dose for evacuation ($ED_{80}$) according to the Litchfield-Wilcoxon method.

After administration of the test samples, the test animals were placed in situation that water could not be taken until finish of the test but feed could be taken freely. For a group for control, the same amount of water for injection was administrated.

Table for Group Construction

| Group | Oral administration (mg/kg) | Number of animals (head) |
|---|---|---|
| Control | 0 | 5 |
| Sample A | 500 | 5 |
| | 1000 | 5 |
| | 2000 | 5 |
| Sample B | 500 | 5 |
| | 1000 | 5 |
| | 2000 | 5 |

$$\text{Water content (\%)} = \frac{W - D}{W - \text{Weight of filter paper}}$$

Statistical Treatment:

From the resultant measured values, an average value and a standard error were calculated for each group. A variance test was made according to the Bartlett method (5%). As variance was found even, the so-called Tukey's test for multiple comparison was carried out. The calculated values were tested according to the Fisher's direct probability calculation method. A value not more than 5% was deemed significant.

Test Results:

Concerning the number of animals excreted diarrhea feces, an animal excreted feces of Score No. 2 was determined as an animal excreted diarrhea feces and the number was counted for each observing period of time (0–2, 2–4, 4–6, and 6–8 hours), referred to hereinafter simply as "observation time", and a result thereof is shown in FIG. 1, while a wet weight of feces collected in every observation time is shown in FIG. 2.

In FIG. 2, a result of Sample A (Example 1) is shown by way of a solid line while that of Sample B is shown by way of a dotted line.

Consideration on the Test Result:

1. Number of Animals Excreting Diarrhea Feces:

In control group, none of all animals was observed to excrete diarrhetic feces over all the observation time up to 8 hours. In case of Samples A and B, no animal was observed that excreted feces of at least Score No. 1 during the observation time up to 2 hours. During the observation time of 2–4 hours, diarrhetic feces were observed in one animal out of the S animals belonging to the group of 500 mg/kg of Sample A, while diarrhetic feces were observed in all animals in the groups of 1000 and 2000 mg/kg, thus making the groups of 1000 and 2000 mg/kg significant to the control group.

In case of Sample B, 2, 4 and 5 animals excreting diarrhetic feces were observed among the groups of 500, 1000 and 2000 mg/kg each consisting of 5 animals, respectively, so that the groups of 1000 and 2000 mg/kg were significant to the control group. The $ED_{50}$ and $ED_{80}$ values were calculated as 587 and 1102 mg/kg, respectively (95% confidence limit: 338–1019 mg).

At an observation time of 4–6 hours, 2, 4 and 3 animals excreting diarrhetic feces were observed among the groups of 500, 1000 and 2000 mg/kg of Sample A each consisting of 5 animals, respectively, so that the group of 1000 mg/kg was significant to the control group. The $ED_{50}$ and $ED_{80}$ values were calculated as 464 and 7052 mg/kg, respectively (95% confidence limit: 66–3249 mg). In case of Sample B, 3, 4 and 5 animals excreting diarrhetic feces were observed among the groups of 500, 1000 and 2000 mg/kg each consisting of 5 animals, respectively, so that the groups of 1000 and 2000 mg/kg show significantly high values to the control group. The $ED_{50}$ and $ED_{80}$ values were calculated as 371 and 1197 mg/kg, respectively (95% confidence limit: 133–1035 mg).

In case of Sample B, the $ED_{50}$ and $ED_{80}$ values were 0.8 and 0.2, respectively, if those values of Sample A were 1. In total of the observation time 0–6 hours, 2, 5 and 5 animals excreting diarrhetic feces were observed among the groups of 500, 1000 and 2000 mg/kg of Sample A each consisting of 5 animals, respectively, thus showing significantly high values in the groups of 1000 and 2000 mg/kg as compared with the control group. In case of Sample B, 3, 5 and 5 animals excreting diarrhetic feces were observed among the groups of 500, 1000 and 2000 mg/kg each consisting of 5 animals, respectively, so that the groups of 1000 and 2000 mg/kg showed significantly high values as compared with the Control group.

At an observation time of 6–8 hours, 4, 3 and 1 animals excreting diarrhetic feces were observed among the groups of 500, 1000 and 2000 mg/kg of Sample A each consisting of 5 animals, respectively, a showing significantly high value in the group of 500 mg/kg as compared with the control group. In case of Sample B, on the other hand, 5, 4 and 3 animals excreting diarrhetic feces were observed among the groups of 500, 1000 and 2000 mg/kg each consisting of 5 animals, showing significant high values in the groups of 500 and 1000 mg/kg as compared with the control group. In total observation time 0–8 hours, animals excreting diarrhetic feces were observed in each group of Samples A and B, showing a significantly high value in each group as compared with the control group.

2. Wet Weight of Feces:

An investigation was made on wet weight of feces collected during each observation time. As compared with 1060 mg of the control group, 854, 840 and 784 mg of wet feces were collected during an observation time of 0–2 hours for the groups of 500, 1000 and 2000 mg/kg of Sample A, respectively, while 717, 695 and 749 mg of feces were collected during the same observation time for the groups of 500, 1000 and 2000 mg/kg of Sample B, respectively, thus showing almost same wet weight.

During an observation time of 2–4 hours, 530 mg of wet feces were collected in case of the control group. In case of Sample A, 1490, 1574 and 4573 mg of wet feces were collected for the groups of 500, 1000 and 2000 mg/kg, respectively, thus showing a tendency of increasing the weight in proportion to increase in the dose used. In particular, the group of 2000 mg/kg was significant to the control group. In case of Sample B, 1607, 2280 and 2265 mg of wet feces were collected for the group of 500, 1000 and 2000 mg/kg, respectively, showing increase in the wet weight but not in proportion to the dose used. No significant difference is found between the control group and the Sample B groups.

During an observation time of 4–6 hours, 886 mg of wet feces were collected in case of the control group. In case of Sample A, 741, 676 and 215 mg of wet feces were collected for the group of 500, 1000 and 2000 mg/kg, respectively, while in the case of Sample B, 832, 869 and 562 mg of wet feces were collected for the group of 500, 1000 and 2000 mg/kg, respectively, thus showing similar wet weights.

During an observation time of 6–8 hours, 522 mg of wet feces were collected in the case of control group. In case of Sample A, 766, 423 and 702 mg of wet feces were collected for the group of 500, 1000 and 2000 mg/kg, respectively, while in the case of Sample B, 451, 391 and 556 mg of wet feces were collected for the group of 500, 1000 and 2000 mg/kg, respectively, thus showing similar wet weights.

3. Water Contents of Feces:

An investigation was made on water contents of feces collected during each observation time. In case of control group, the water content of the feces collected during the observation time of 0–2 hour was 58.1%. In case of Sample A, the water contents were 59.7%, 60.2% and 61.9% for the groups of 500, 1000 and 2000 mg/kg, respectively, while in case of Sample B, the water contents were 57.7%, 60.4% and 59.1% for the groups of 500, 1000 and 2000 mg/kg, respectively, showing similar water contents.

In case of the control group, the water contents of feces collected during the observation time of 2–4 hours were 58.4%. In case of Sample A, the water contents were 54.8%, 64.7% and 73.4% for the groups of 500, 1000 and 2000 mg/kg, respectively, thus showing increase in the contents in proportion to increase in the dose used as compared with the control group. The increase in the contents with respect to the group of 2000 mg/kg was significant as compared with the control group. In case of Sample B, the water contents were 58.7%, 62.8% and 66.3% for the groups of 500, 1000 and 2000 mg/kg, respectively, showing increase in the water contents but the increase not being significant.

Example 2

Prescription of Ingredients:

| | |
|---|---|
| Magnesium oxide (BET value: 30) | 66.5% by weight |
| Carboxymethylcellulose calcium | 8.0% by weight |
| Carboxymethylcellulose sodium | 0.8% by weight |
| Magnesium stearate (lubricating agent) | 2.0% by weight |
| A mixture of sporolactobacteria and yeast extracts* | 22.7% by weight |

*A mixture of yeast extract with 1% *Sporolactobacillus acidophius* was used.

In the same procedure as described in Example 1, granules were prepared from the aforesaid ingredients, the resultant granules were shaped into tablets (440 mg/tablet) by the aid of a tableting machine.

The resultant tablets were used for examining evacuating effect of human by oral administration. Eight tablets were forced to take at night before sleeping by ladies of 23, 28, 42, 45 and 60 years old suffering from costiveness as volunteers and in the next morning the ladies were forced to receive a hearing test as to evacuation and odor of feces. As a result of the test, it was reported that except a lady of 45 years old, all of the examined ladies had smooth evacuation about 10 hours after administration of the tablets without bellyache and scarcely felt odor of feces.

The lady of 45 years old showing no evacuating effect was again forced to have 6 tablets orally taken at night of the tested day before sleeping. As a result, it was reported that the lady had smooth evacuation about 10 hours after administration and felt scarcely odor of feces.

Example 3

In Example 2, tablets were prepared in the same manner as described in Example 2 except one or more of the following lactic acid bacteria were used in place of the mixture of sporolactobacteria and yeast extracts: *Bifidobac-* terium longum, Lactobacillus salivalius, and Lactobacillus fermentium and a similar test was carried out for 5 volunteers. As a result of the test, it was reported that all 5 volunteers had smooth evacuation without bellyache and felt scarcely odor of feces.

Example 4

In the same test as described above, 5 volunteers were forced to elect tablets containing either one of the above lactic acid bacteria and then forced to take 6 tablets (dose reduced by 2 tablets) for consecutive one month. After one month, it was reported that all volunteers had smooth evacuation without bellyache and felt almost no odor in feces.

Example 5

To 85 milliliters of water was added 2.4 g of magnesium oxide (BET value: 30), and the mixture was admixed with 15 ml of 90% fermentation lactic acid. As the magnesium oxide is rapid in acid reactivity with fermentation lactic acid, the former was easily soluble in the latter whereby a solution of magnesium lactate was obtained easily. When the resultant active magnesium lactate solution was orally administered to 5 volunteers as shown in Example 2 in a dose of 70 ml/day, the same evacuating effect as described in Example 2 was reported. It is also reported that the liquid preparations could favorably be administered orally.

Example 6

A liquid preparation (elixir) was prepared by mixing 100 ml of an active magnesium lactate solution obtained in Example 5 with 100 ml of an oligosaccharide solution and 40 ml of a prune drink. In the same manner as described in Example 5, this liquid preparation was given to 5 volunteers in a dose of 150 ml/day. It was then reported that this liquid preparation was more smooth in evacuation effect and more easily drinkable than the preparation described in Example 5.

Thus, the evacuant concerned with the present invention can be used as safe and useful medical preparations with excellent pharmacological effects.

It is understood that preceding representative examples may be varied within the scope of the present specification, both as to the ingredients and conditions, by those skilled in the art to achieve essentially the same results.

As many apparently widely different embodiments of the present invention may be made without departing from the spirit and scope thereof, it is to be construed that the present invention is not limited to the specific embodiments thereof as defined in the appended claims.

What is claimed is:

1. An evacuant comprising magnesium oxide having a BET value of at least 21 $m^2/g$ as an effective ingredient, a binder and a disintegrating agent.

2. An evacuant according to claim 1, wherein the BET value of magnesium oxide is in the range of 21 to 50 $m^2/g$.

3. An evacuant according to claim 1, wherein the BET value of magnesium oxide is in the range of 30–40 $m^2/g$.

4. An evacuant according to claim 1, wherein the evacuant further contains one or more lactic acid bacteria.

5. An evacuant according to claim 4, wherein the lactic acid bacteria are selected from at least one of *Lactobacillus lactis, Bifidobacterium longum, Bifidobacterium bifidum, Lactobacillus acidophilus, Lactobacillus salivalius, Lactobacillus fermentium* and *sporolactobacteria*.

6. An evacuant according to claim 5, wherein the sporolactobacteria are in the form of a mixture with yeast extracts.

7. An evacuant according to claim 1 or claim 4, wherein the evacuant further contains an oligosaccharide.

8. An evacuant according to claim 1 or claim 4, wherein the evacuant further contains phenolphthalein.

9. An evacuant according to claim 1 or claim 4, wherein the evacuant is in the form of a liquid preparation in which the magnesium oxide has been dissolved in L-form fermentation lactic acid.

10. An evacuant according to claim 1 or claim 4, wherein the evacuant is in the form of powder, granules obtained according to a dry granulation method or wet granulation method, or tablets obtained by compressing the powder or granules.

11. An evacuant according to claim 10, wherein the evacuant is in the form of capsule preparations obtained by charging the capsule with the powders or granules obtained according to the dry granulation method or wet granulation method.

12. An evacuant according to claim 11, wherein the wet granulation method employs an alcohol.

13. An evacuant according to claim 1 or claim 4, wherein the evacuant is further incorporated with an oral refresher.

14. An evacuant according to claim 5, wherein the sporolactobacteria is *Sporolactobacillus inulinis*.

15. An evacuant comprising magnesium oxide having a BET value of at least 21 $m^2/g$ as an effective ingredient and one or more lactic acid bacteria.

16. evacuant according to claim 15, wherein the lactic acid bacteria are selected from at least one of *Lactobacillus lactis, Bifidobacterium longum, Bifidobacterium bifidum, Lactobacillus acidophilus, Lactobacillus salivalius, Lactobacillus fermentium,* and *sporolactobacteria*.

17. An evacuant according to claim 16, wherein the sporolactobacteria are in the form of a mixture with yeast extracts.

18. An evacuant according to claim 15, wherein the evacuant further contains an oligosaccharide.

19. An evacuant according to claim 15, wherein the evacuant further contains phenolphthalein.

20. An evacuant according to claim 15, wherein the evacuant is in the form of a liquid preparation in which the magnesium oxide has been dissolved in L-form fermentation lactic acid.

21. An evacuant according to claim 15, wherein the evacuant is in the form of powder, granules obtained according to a dry granulation method or wet granulation method, or tablets obtained by compressing the powder or granules.

22. An evacuant according to claim 21, wherein the evacuant is in the form of capsule preparations obtained by charging the capsule with the powders or granules obtained according to the dry granulation method or wet granulation method.

23. An evacuant according to claim 22, wherein the wet granulation method employs an alcohol.

24. An evacuant according to claim 15, wherein the evacuant is further incorporated with an oral refresher.

25. An evacuant according to claim 15, wherein the sporobacteria is *Sporolactobacillus inulinis*.

* * * * *